United States Patent [19]
Miles

[11] Patent Number: 5,153,671
[45] Date of Patent: Oct. 6, 1992

[54] GAS ANALYSIS SYSTEM HAVING BUFFER GAS INPUTS TO PROTECT ASSOCIATED OPTICAL ELEMENTS

[75] Inventor: Scott D. Miles, Sandy, Utah

[73] Assignee: BOC Health Care, Inc., Murray Hill, N.J.

[21] Appl. No.: 522,533

[22] Filed: May 11, 1990

[51] Int. Cl.⁵ .......................... G01J 3/44; G01N 21/65
[52] U.S. Cl. .................................... 356/301; 356/338; 356/246
[58] Field of Search ............... 356/301, 246, 410, 440, 356/338, 339, 437, 438, 439; 350/584

[56] References Cited

U.S. PATENT DOCUMENTS

| | | |
|---|---|---|
| 3,515,482 | 6/1970 | Garrow et al. |
| 3,833,305 | 9/1974 | Porter et al. |
| 4,071,298 | 1/1978 | Falconer ............................ 356/301 |
| 4,113,386 | 9/1978 | Lepper, Jr. |
| 4,225,243 | 9/1980 | Typpo ............................. 356/409 |
| 4,277,131 | 7/1981 | Hart et al. |
| 4,413,911 | 11/1983 | Rice et al. ........................ 356/438 |
| 4,443,072 | 4/1984 | Ballard ............................. 356/246 |
| 4,515,274 | 5/1985 | Hollinger et al. .................. 356/246 |
| 4,544,273 | 10/1985 | Berndt ............................. 356/434 |
| 4,594,715 | 6/1986 | Knollenberg ....................... 372/32 |
| 4,647,780 | 3/1987 | Dunkel ............................ 250/573 |
| 4,648,714 | 3/1987 | Benner et al. ..................... 356/301 |
| 4,649,830 | 3/1987 | Tanaka . |
| 4,654,226 | 3/1987 | Jackson et al. |
| 4,672,620 | 6/1987 | Slusher et al. ..................... 372/58 |
| 4,676,639 | 6/1987 | Van Wagenen ..................... 356/246 |
| 4,701,096 | 10/1987 | Fisher, Jr. |
| 4,713,964 | 12/1987 | Ioannides ......................... 356/439 |
| 4,723,063 | 2/1988 | Armier et al. |
| 4,746,215 | 5/1988 | Gross ............................. 356/246 |
| 4,784,486 | 11/1988 | Van Wagenen et al. ............. 356/301 |
| 4,784,491 | 11/1988 | Penney et al. ..................... 356/376 |
| 4,786,188 | 11/1988 | Myhre et al. |
| 4,787,750 | 11/1988 | Nelson et al. |
| 4,837,443 | 6/1989 | Young et al. |
| 4,840,226 | 6/1989 | Richlen . |
| 4,845,426 | 7/1989 | Dickson et al. |
| 4,846,102 | 7/1989 | Ozias . |
| 4,924,097 | 5/1990 | Browner et al. .................... 356/301 |
| 4,940,327 | 7/1990 | Lilienfield ........................ 356/338 |
| 4,983,038 | 1/1991 | Ohki et al. ....................... 356/246 |
| 5,011,286 | 4/1991 | Petralli .......................... 356/338 |

FOREIGN PATENT DOCUMENTS

| | | |
|---|---|---|
| 2061491 | 6/1971 | France . |
| 2210291 | 7/1974 | France . |
| 60-233536 | 11/1985 | Japan . |
| 1376011 | 2/1988 | U.S.S.R. ......................... 356/246 |

*Primary Examiner*—F. L. Evans
*Attorney, Agent, or Firm*—Dennis Epperson; Roger M. Rathbun; Larry R. Cassett

[57] ABSTRACT

A gas analysis cell positioned within an optical resonant cavity in a gas analysis system is disclosed wherein the cell includes a flow of buffer gas which forms a "dam", thereby protecting the optical elements in the analysis system. The analysis cell includes an inlet for introducing a gas sample into the analysis chamber of the cell. Two buffer gas inlet ports, one on each end of the cell, are provided to introduce a flow of buffer gas which is directed past optical elements in the system adjacent the ends of the cell. Two output ports are located at the ends of the analysis chamber to remove the buffer gas and gas sample mixture. The flow of buffer gas acts to confine the gas sample within the analysis chamber and reduce adverse effects which occur when the gas sample comes in contact with the optical elements of the system. By providing a constant non-turbulent flow of gas adjacent the system optics, adverse changes in index of refraction are avoided, thus reducing beam steering and Schlieren effects which can occur when Brewster windows or other optics are used to constrain the gas sample within the analysis cell. The buffer gas flow in the analysis cell of the present invention eliminates the need for gas cell windows which have intrinsic losses. This in turn minimizes losses which cause lower circulating intracavity power and signal strength.

12 Claims, 2 Drawing Sheets

GAS ANALYSIS SYSTEM HAVING BUFFER GAS INPUTS TO PROTECT ASSOCIATED OPTICAL ELEMENTS

FIELD OF THE INVENTION

The invention relates to a gas analysis cell, and, in particular, to a gas analysis cell for containing a gas sample in a laser Raman gas analysis system.

BACKGROUND OF THE INVENTION

Raman light scattering has been successfully used in critical care situations to continuously monitor a patient's respiratory gases. This technique is based on the effect which occurs when monochromatic light interacts with vibrational/rotational modes of gas molecules to produce scattered light which is frequency shifted from that of the incident radiation by an amount corresponding to the vibrational/rotational energies of the scattering gas molecules. If the incident light photon loses energy in the collision, it is re-emitted as scattered light with lower energy and consequently lower frequency than the incident photon. In a similar manner, if the incident photon gains energy in the collision, it is re-emitted as scattered light with higher energy and higher frequency than the incident photon. Since these energy shifts are species-specific, analysis of the various frequency components present in the Raman scattering spectrum of a sample provides chemical identification of the gases present in the scattering volume. The intensity of the various frequency components or Raman spectral lines provides quantification of the gases present, providing suitable calibrations have been made. In this manner, Raman light scattering can be employed to determine the identity and quantity of various respiratory and anesthetic gases present in a patient's breath in operating room and intensive care situations.

In addition to critical care situations, Raman light scattering gas analysis can also be used in many industrial applications such as stack gas analysis for combustion control, process control, fermentation monitoring, and pipeline gas mixture control. This analysis technique can also be extended to meet environmental monitoring needs in many areas such as escaped anesthetic agents in the operating room, air pollution, auto emissions testing and submarine atmosphere monitoring.

Systems developed for analysis of gases in critical care situations utilizing Raman scattering typically employ gas cells which contain a sample of the patient's respiratory gas to be analyzed. The gas sampling cell is located either within the resonant cavity of a laser or outside the cavity. In an intracavity system, a laser beam is directed through the resonant cavity such that it intercepts the gas within the sampling cell. Raman scattered light from the gas analysis region within the cell is collected by a collection optic and directed through one or more interference filters. The collection optics and interference filters and possibly focusing optics in turn transmit the Raman scattered light to appropriate detectors for quantitating each specific Raman signal, and thus, each specific gas comprising the respiratory sample.

Windows are commonly provided on either end of the gas sampling cell to protect surrounding optical elements and filters from contaminants which may be present in the gas sample. The windows further serve to confine the gas sample within the chamber, minimizing the volume of the sample and thus improving response time. In some systems, the gas cell windows can be oriented at brewster's angle to select and improve the transmission of a particular polarization of light passing through the sample. In this manner, optical losses in the laser beam which passes through the cell are minimized. However, the gas sample, in combination with particulates often carried with the sample, contaminates the cell windows and degrades the performance of the system. For example, this contamination may result in undesirable light scattering, and thus, the electrical power, and correspondingly, the laser current, required to maintain the laser light intensity is greatly increased. If untreated and uncorrected, the system will cease to function properly. Current respiratory gas analysis systems require replacement or cleaning of the gas cell to compensate for the accumulation of contaminants. This is generally a time-consuming process which involves not only the replacement or cleaning of the cell, but also, recalibration of the system, both at substantial expense in both time and money.

SUMMARY OF THE INVENTION

In accordance with one embodiment of the present invention, a gas analysis cell is located within the resonant cavity of a laser in a gas analysis system. The ends of the resonant cavity are defined by two reflectors, preferably in the form of high reflectivity mirrors, gratings, or other known reflective elements. A sample of the gas to be analyzed is admitted to an analysis chamber within the analysis cell and a laser beam is directed through the analysis chamber such that the beam intercepts the gas sample therein. Raman scattered light is collected in detector channels adjacent the analysis chamber and analyzed with signal processing means in order to determine the type and quantity of the various gases comprising the sample.

The gas analysis cell of the present invention includes in addition to a sample input port, two input ports through which a flow of buffer gas is introduced. The flow of buffer gas is directed past optical elements on either end of the analysis cell. Two output ports are located on the ends of the analysis chamber to remove both the buffer gas and gas sample. The buffer gas flow acts to effectively confine the sample gas within the analysis region of the chamber and prevents the gas sample from contacting and contaminating the mirrors and any other optical elements in the cavity. Since no exposure of the optical elements to the gas sample occurs, the detrimental effects of the sampled gas upon the system optics are prevented. In addition, the constant, non-turbulent flow of buffer gas reduces the variation in density gradients of the gas flow within the gas cell, thereby reducing adverse effects such as beam steering and Schlieren effects which result from abrupt changes in refractive index caused by varying density gradients in the gas flow along the optical path of the light beam.

The present invention provides a gas analysis system comprising a cavity having an optical element wherein the cavity is capable of propagating a beam of optical radiation. A gas cell is positioned within the cavity and adapted to receive a gas sample. The gas cell is further configured to permit the beam to pass through the gas sample. A buffer gas inlet port is coupled to the cavity for introducing a flow of buffer gas to the cavity wherein the flow of buffer gas substantially prevents the gas sample from contacting the optical element. The cavity may be a resonant cavity. In addition, the resonant cavity may be a lasing cavity adapted for the amplification of light. The gas cell may further comprise at least one light output channel for transporting light which is scattered out of the beam of optical radiation by the gas sample. The analysis system may also include an outlet port coupled to the resonant cavity for removing gases from the gas cell and the cavity. The buffer gas inlet port may be constructed and arranged so that buffer gas floods a region adjacent the optical element. Also, the buffer gas inlet port may be constructed and arranged so that the flow of buffer gas into the cavity is non-turbulent.

An apparatus for the analysis of a gas sample is disclosed comprising a laser light source for producing a laser beam. The laser source comprises a resonant cavity and a lasing medium located within the resonant cavity. A gas cell is positioned within the resonant cavity. The gas cell comprises a housing and an analysis chamber enclosed within the housing. A sample gas inlet port is formed in the housing for introducing a gas sample into the analysis chamber and a buffer gas inlet port is formed in the housing for receiving a flow of buffer gas. A gas outlet port is formed in the housing wherein the outlet port provides an outlet for the buffer gas and the gas sample in a manner which substantially confines the sample gas to a region of the analysis chamber located intermediate the sample gas inlet port and the gas outlet port. The analysis chamber may further comprise at least one light output channel for transporting light which is scattered out of the laser beam by the gas sample.

In accordance with the present invention, a gas analysis system is disclosed comprising a laser having a longitudinal resonant cavity wherein the ends of the cavity are defined by first and second high reflectivity mirrors. A gas analysis cell is positioned within the resonant cavity intermediate the mirrors and comprises an analysis chamber having a first end and a second end. A sample gas inlet port is located intermediate the analysis chamber first and second ends for introducing a gas sample into the analysis chamber. First and second buffer gas inlet ports are located at the first and second ends of the analysis chamber for introducing a flow of buffer gas into the analysis cell. First and second outlet ports are located near the first and second ends of the analysis chamber for removing the gases from the analysis cell such that the flow of buffer gas between the buffer gas inlet ports and the outlet ports confines the gas sample to the analysis chamber.

A method for constraining a gas sample within a gas analysis cell located within a cavity is disclosed comprising the steps of introducing the gas sample into the analysis cell and introducing a flow of buffer gas into the analysis cell such that the flow of buffer gas through the cell substantially confines the gas sample within the analysis cell.

The present invention provides a device for the analysis of gases in a gas sample utilizing Raman light scattering comprising an optical cavity and a gas analysis chamber for receiving a gas sample. The chamber is positioned within the optical cavity and in fluid communication with at least a portion of the cavity located outside the analysis chamber. The device may further comprise a gas dam for substantially constraining the gas sample to the analysis chamber.

DETAILED DESCRIPTION OF THE INVENTION

Figure 1:
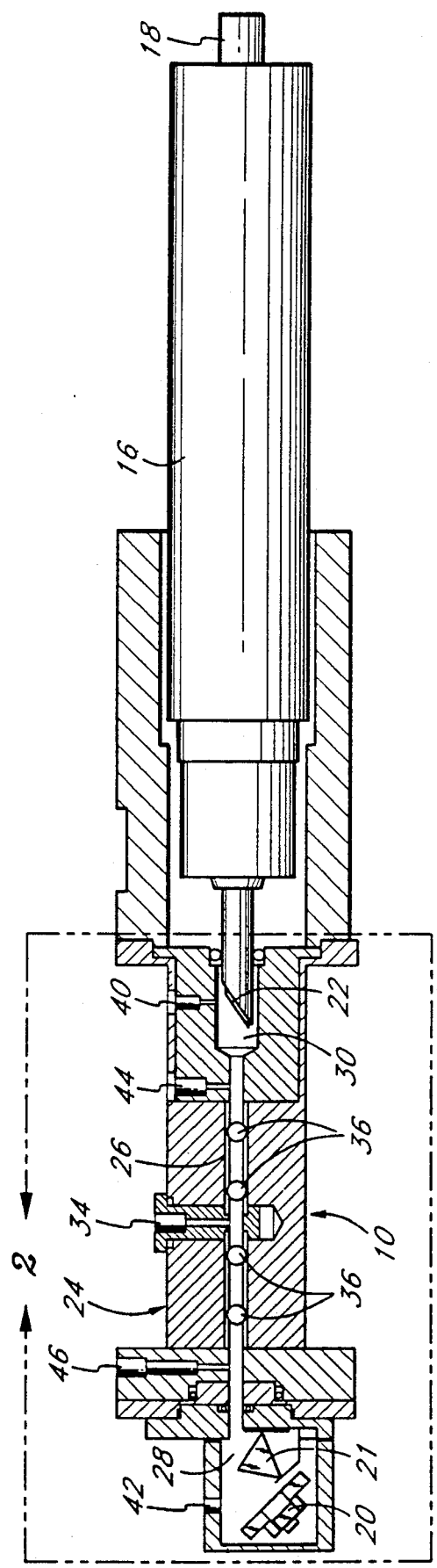
FIG. 1 illustrates a gas analysis cell within a laser resonant cavity in a gas analysis system in a first embodiment of the present invention.

As shown in FIG. 1, a gas analysis cell 10 in accordance with the present invention is positioned within a resonant cavity of a laser in a gas analysis system. The resonant cavity includes a plasma discharge tube 16 and has a volume which is defined by a first reflector 18 and a second reflector 20. The first reflector 18 preferably comprises a high reflectivity mirror, i.e., a mirror with a reflectivity greater than 99.99%. The reflector 20 preferably comprises a second high reflectivity mirror. Alternatively, the second high reflectivity mirror could be coated on the back side of a Littrow prism. A Brewster prism 21 may be inserted in the cavity to select a particular wavelength of light for circulation through the resonant cavity. A lasing gas mixture is confined within the discharge tube 16 and a Brewster window 22 is positioned at the end of the discharge tube 16 adjacent the output such that the light beam propagating within the cavity enters and exits the discharge tube 16 through the Brewster window 22.

Figure 2:
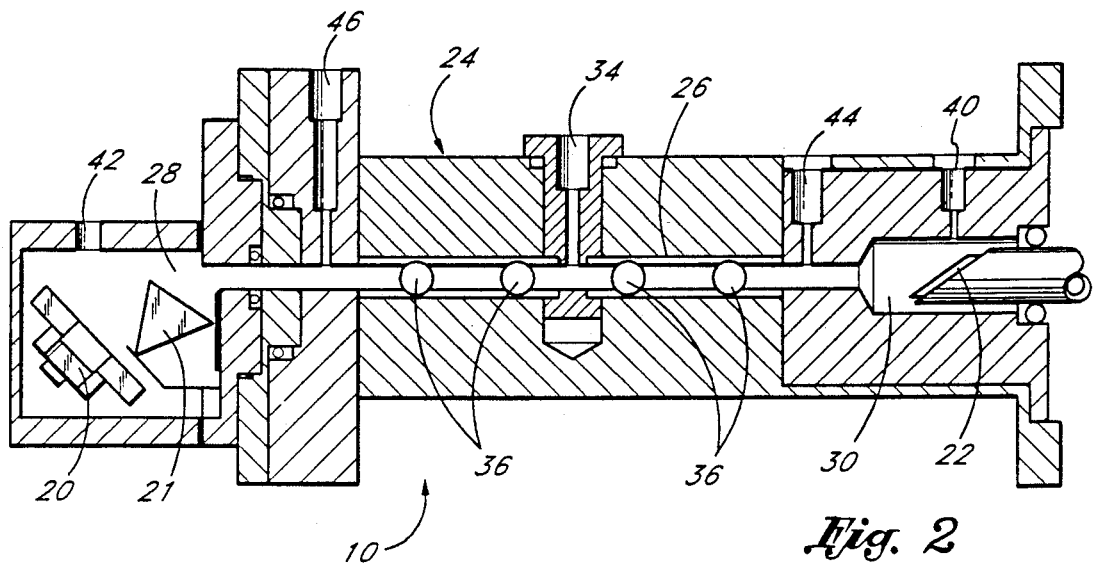
FIG. 2 is an enlarged view of the gas analysis cell of the present invention.

Referring to FIG. 1 and FIG. 2, the gas analysis cell 10 is positioned intermediate the Brewster window 22 and second reflector 20 within the laser resonant cavity. The analysis cell 10 comprises a housing 24 enclosing an analysis chamber 26. The analysis cell 10 includes two buffer regions 28, 30 on either end of the analysis chamber 26. The analysis chamber 26 is connected to the source of gas to be analyzed by a gas sample inlet port 34. The gas analysis cell 10 further comprises a plurality of output channels 36 which form optical passageways between the analysis chamber 26 and the outside of the gas cell 10. A first buffer gas input port 40 is connected to the buffer region 30 adjacent the Brewster window 22 and a second buffer gas input port 42 is connected to the buffer region 28 adjacent the second reflector 20. In addition, the cell comprises a first output port 44 connected to the buffer region 30 at the end of the analysis chamber 26 nearest the Brewster window 22. Output port 44 is positioned intermediate the gas sample inlet port 34 and first buffer gas inlet port 40. A second output port 46 is connected to the buffer region 28 at the end of the analysis chamber nearest the second reflector 20. Output port 46 is positioned intermediate the gas sample inlet port 34 and the second buffer gas inlet port 42.

A gas sample which is to be analyzed enters the sampling cell 10 through the input port 34 and is contained within the analysis chamber 26. The laser discharge tube 16 emits a collimated beam of polarized light with a characteristic wavelength dependent upon the type of gas within the discharge tube 16 the orientation of the Brewster prism 21, and the nature of the mirror coating on high reflector mirrors 18,20. The light beam travels an optical path through the Brewster window 22 and through the length of the analysis chamber 26 of the gas analysis cell 10 and is incident upon the second reflector 20. The length of the resonant cavity is such that the light beam resonates between the first and second reflectors 18, 20 which define the volume of the resonant cavity. Thus, the emitted light propagates within the resonant cavity, entering and exiting the discharge tube 16 through the Brewster window 22, thereby stimulating further emission of additional excited atoms within the discharge tube and achieving optimum light amplification. The Brewster prism 21 optimizes the power of a preferred wavelength and polarization state of the laser beam circulating in the resonant cavity. Thus, the Brewster window 22 serves to seal the gas within the discharge tube 16 while also providing polarization control of the light beam by completely transmitting light of a preferred polarization state.

Inside the analysis chamber 26 of the sampling cell 10, the light beam circulating in the resonant cavity intercepts the sample of the gas to be analyzed. The Raman scattered radiation from the gas sample is collected over as large a solid angle as possible by the detector channels 36, which are located approximately perpendicular to and on either side of the axis of the laser light beam propagating inside the analysis chamber 26. The Raman signals can then by analyzed with a microprocessor (not shown) associated with the detector channels 36 and, based on this analysis, the identity and concentration of each specific gas comprising the gas sample contained within the analysis chamber 26 can be determined and reported. A more detailed description of this analysis process can be found in U.S. Pat. No. 4,784,486 entitled "Multi-Channel Molecular Gas Analysis by Laser-Activated Raman Light Scattering", assigned to the assignee of the present invention and incorporated herein by reference.

Figure 2A:
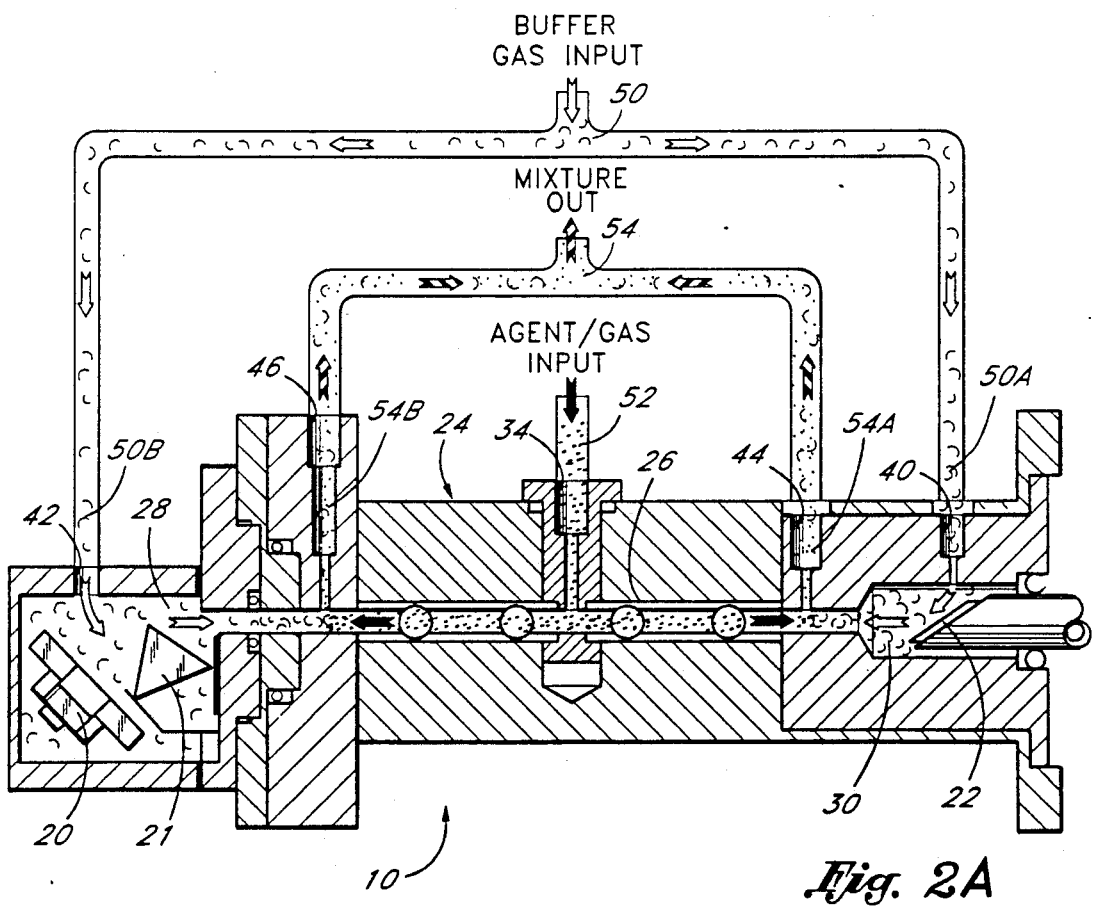
FIG. 2A is an enlarged view of the gas cell of the present invention illustrating the ga flows within the cell.

Referring to FIG. 2A, a flow of buffer gas 50 is introduced into the two buffer gas inlet ports 40, 42 formed in the buffer regions 28, 30 of the cell 10. A portion 50A of the flow 50, input through the first buffer gas inlet port 40, is directed past the Brewster window 22 and toward one end of the analysis chamber 26. A second portion 50B of the flow 50, input through the second buffer gas inlet port 42, is directed past the end reflector 20 and toward the opposing end of the analysis chamber 26. Near the openings in the ends of the analysis chamber 26, the buffer gas flows 50A and 50B mix with the gas sample 52 contained within the analysis chamber 26 and forms gas mixtures 54A and 54B. The gas mixtures 54A and 54B then exit the gas analysis cell 10 through the output ports 44, 46 formed in the housing 24 at either end of the analysis chamber 26. Thus, the buffer gas flow 50 through the analysis cell 10 forms a "dam" which constrains the gas sample 52 to the portion of the analysis chamber 26 located intermediate the analysis chamber outlet ports 44, 46. In this manner, the buffer gas flows 50A and 50B serve to protect the optical elements, i.e., the Brewster window 22, the second reflector 20, and the Brewster prism 21, of the gas analysis system from contaminants which may be present in the gas sample 52. This is a significant improvement over typical prior art gas analysis systems in which additional Brewster windows are mounted at each end of the chamber 26 to contain the gas sample 52 within the analysis chamber 26 and protect the remaining optical elements in the cavity from the detrimental effects of the gas sample. Such windows are themselves subject to contamination from the gas sample 52, resulting in laser power losses. Such windows also have intrinsic loss mechanisms which detract from the maximum attainable circulating optical power in the laser resonator. The flow of buffer gas 50A and 50B through the analysis cell 10 eliminates the need for any windows at the ends of the analysis chamber 26, thus maximizing the circulating optical power in the resonant cavity.

In addition to protecting the optics 20, 21, 22 from contaminants in the gas sample 52, the gas analysis cell 10 illustrated in FIG. 1 and FIG. 2 further serves to reduce problems caused by variations in index of refraction and beam steering which often occur as the laser beam propagates through the Brewster window 22. When the laser beam passes through the Brewster window 22 adjacent the discharge tube 16, it is "steered", i.e., deflected, and exits the Brewster window 22 at an angle which is different from the angle at which it entered if the index of refraction of the gases on the two sides of the window are not equal. The angle in reference to the axis of the resonant cavity at which the laser beam emitted from the discharge tube 16 exits the Brewster window 22 is dependent upon 1) The indices of refraction of the window material and the gases on either side of the window; and 2) The angle of the plane in which index of refraction changes occur relative to the axis of the laser beam passing through the analysis cell 10. Note, that if this plane is perpendicular to the beam axis, no change in beam direction will occur regardless of differences in indices of refraction. Obviously, the index of refraction of the window material comprising the Brewster window 22 is fixed. However, the index of refraction of the sample gas on the gas cell side of the window will change as the individual components comprising the gases vary in type and concentration.

With the gas cell 10 of the present invention, the buffer gas flow 50A shown in FIG. 2A immediately in front of the Brewster window 22 along the optical path of the light beam remains constant regardless of what type and concentration of gases comprising the gas sample 52 are introduced into the analysis chamber 26. Since the index of refraction does not change next to the side of the Brewster window 22 adjacent the analysis chamber 26, the angle at which the beam exits the Brewster window is constant and beam steering effects due to the buffer gas are predictable and can be accounted for in the design. One skilled in the art will recognize that the index of refraction of the gas sample 52 contained in the analysis chamber 26 of the gas cell still varies as the concentration of the individual gases comprising the sample varies, and thus, the index of refraction changes where the sample gas mixes with the buffer gas 50 creating the gas mixture 54. However, this change in index of refraction occurs in a plane which is nominally perpendicular to the optical path of the laser beam and hence, does not cause the beam steering problems which occur when the change in refractive index occurs at Brewster window 22, i.e., in a plane which is not perpendicular to the optical path. Furthermore, the buffer gas flow 50 can be utilized not only to prevent beam steering, but also to move unavoidable beam steering effects to a location where the effects are no longer deleterious.

Although the analysis chamber inlet port 34 need not be positioned in the center of the analysis cell as illustrated in FIG. 1 and FIG. 2, there are several advantages associated with this location. When the gas sample 52 is introduced in the center of the gas analysis cell 10, the flow is introduced immediately into the analysis chamber 26 without having to displace the volumes around the optics 20, 22 at either end of the cell. In addition, in analysis systems wherein the gas sample is introduced into one end of the analysis chamber 26, the gas sample flows past each pair of detector channels 36 sequentially. In the analysis cell 10 of the present invention, the gas sample 52 flows into the center of the analysis chamber 26 and then flows away from the inlet 34 in two directions, toward each end of the chamber 26. When input in this manner, two pairs of detector channels 36 are located immediately adjacent to the gas sample input 34, thereby advantageously decreasing response time by as much as one half compared with the response time of prior art systems wherein the gas sample 52 is introduced at one end of the analysis chamber 26.

When the buffer gas flow 50 is input at relatively low flow rates, the flow generally is laminar rather than turbulent in nature. Thus, the point inside the analysis cell 10 at which the gas sample 52 mixes with the buffer gas 50 to form the gas mixture 54 occurs in the laminar flow region, thereby eliminating turbulent mixing and changes in refractive index, i.e., Schlieren effects which can cause power losses in the transmission of the laser beam.

Although the invention has been described in terms of preferred embodiments, it will be apparent to those skilled in the art that numerous modifications can be made without departing from the spirit and scope of the claims appended hereto. Such modifications are intended to be included within the scope of the claims.

I claim:

1. A gas analysis system comprising:
   a light source for producing optical radiation;
   a cavity having an optical element, said cavity capable of propagating said optical radiation produced by said light source;
   an analysis chamber having a sample interaction region, said analysis chamber positioned within said cavity and adapted to receive a gas sample, said chamber configured to permit said optical radiation to pass through at least a portion of said gas sample located in said sample interaction region;
   a buffer gas inlet port coupled to said cavity for introducing a flow of buffer gas to said cavity, wherein said flow of buffer gas substantially prevents said gas sample from contacting said optical element;
   a gas outlet port for removing said sample gas and said buffer gas from said cavity and preventing penetration of said buffer gas into said sample interaction region; and
   a detector channel for sensing optical radiation scattered into said channel by said portion of said gas sample located in said sample interaction region of said analysis chamber, wherein said detector channel, said buffer gas inlet port, and said buffer gas outlet port cooperatively prevent the sensing of any optical radiation scattered by said gas sample which has propagated through any region containing buffer gas along its path from said sample interaction region to said detector channel.

2. A gas analysis system as defined in claim 1, wherein said cavity is a lasing cavity adapted for the amplification of light.

3. A gas analysis system as defined in claim 1 wherein said buffer gas inlet port is constructed and arranged so that buffer gas floods a region adjacent said optical element.

4. A gas analysis system as defined in claim 1 wherein said buffer gas inlet port is constructed and arranged so that the flow of buffer gas into the cavity is non-turbulent.

5. A gas analysis system as defined in claim 1, wherein said cavity is a resonant cavity.

6. An apparatus for the analysis of a gas sample comprising:
   a laser light source for producing a laser beam, said laser source comprising:
      a resonant cavity; and
      a lasing medium located within said resonant cavity; and
   a gas cell positioned within said resonant cavity, said gas cell comprising:
      a housing;
      an analysis chamber within said housing, said analysis chamber having a sample interaction region;
      a sample gas inlet port formed in said housing for introducing a gas sample into said analysis chamber and sample interaction region;
      a buffer gas inlet port formed in said housing for receiving a flow of buffer gas;
      a bas outlet port formed in said housing wherein said outlet port provides an outlet for said buffer gas and said gas sample in a manner which substantially prevents mixing of the sample gas and the buffer gas in said sample interaction region; and
      a light output channel for transporting light which is scattered out of said laser beam by said gas sample in said sample interaction region, said light output channel configured so that it prevents the transport of light scattered by said sample gas which, after scattering from said sample gas, propagates through any region containing buffer gas.

7. A gas analysis system as defined in claim 6, further comprising a detector for sensing light which has propagated through said light output channel.

8. A gas analysis system comprising:
   a laser, said laser having a longitudinal resonant cavity for propagating a light beam, wherein the ends of said cavity are defined by first and second high reflectivity mirrors;
   a gas analysis cell positioned within said resonant cavity intermediate said mirrors, said gas analysis cell comprising:
      an analysis chamber having a first end, a second end, and an interaction region;
      a sample gas inlet port located intermediate said analysis chamber first and second ends for introducing a gas sample into said analysis chamber and interaction region;
      first and second buffer gas inlet ports located at said first and second ends of said analysis chamber for introducing a flow of buffer gas into said analysis cell; and
      first and second outlet ports located at said first and second ends of said analysis chamber for removing said buffer and sample gases from said analysis cell such that the flow of buffer gas between said buffer gas inlet ports and said outlet ports confines said gas sample to said analysis chamber substantially prevents mixing of said sample gas and said buffer gas in said interaction region; and
   a detector for sensing light scattered out of said light beam by said gas sample in said interaction region, wherein the path of said scattered light from said interaction region to said detector does not traverse any region containing said buffer gas.

9. A method for constraining and analyzing a gas sample within a gas analysis cell having a sample interaction region, said method comprising the steps of:

introducing said ga sample into said gas analysis cell and sample interaction region;

introducing a flow of buffer gas into said analysis cell such that said flow of buffer gas through said gas analysis cell substantially confines said gas sample within said gas analysis cell and substantially prevents mixing of said buffer gas and said sample gas within said sample interaction region;

illuminating said gas sample with electromagnetic radiation; and collecting and detecting electromagnetic radiation scattered by said gas sample in said sample interaction region such that the only scattered electromagnetic radiation which is detected traverses a path from said sample interaction region through regions containing pure sample gas.

10. A device for the analysis of gases in a gas sample utilizing light scattering, comprising:

a light source;

an optical cavity which propagates light produced by said light source;

a gas analysis chamber for receiving a gas sample, said chamber including a sample interaction region, wherein said chamber is positioned within said optical cavity and in fluid communication with at least a portion of said cavity located outside said analysis chamber;

a buffer gas inlet port for introducing buffer gas into said gas analysis chamber but not into said sample interaction region of said analysis chamber, thereby creating in said sample interaction region a region of pure sample gas;

a detector for sensing light scattered from said gas sample in said sample interaction region of said gas analysis chamber, wherein said sensed scattered light traverses a path from the sample gas scattering location to the detector which is devoid of said buffer gas.

11. A device as claimed in claim 10 further comprising a gas dam for substantially constraining said gas sample to said analysis chamber.

12. A gas analysis system as defined in claim 10, wherein said optical cavity is a resonant cavity.

* * * * *